United States Patent
Latour, Jr.

(10) Patent No.: US 6,558,312 B2
(45) Date of Patent: May 6, 2003

(54) INTRAURETHRAL DEVICE FOR INCONTINENCE

(75) Inventor: Robert A. Latour, Jr., Clemson, SC (US)

(73) Assignee: Clemson University, Clemson, SC (US)

(*) Notice: Subject to any disclaimer, the term of this patent is extended or adjusted under 35 U.S.C. 154(b) by 0 days.

(21) Appl. No.: 09/805,581

(22) Filed: Mar. 13, 2001

(65) Prior Publication Data

US 2002/0133053 A1 Sep. 19, 2002

(51) Int. Cl.[7] .............................. A61F 2/00; A61F 5/48; B29C 31/06
(52) U.S. Cl. ........................ 600/29; 128/885; 264/264
(58) Field of Search ...................... 128/885; 264/264; 600/29

(56) References Cited

U.S. PATENT DOCUMENTS

| | | | |
|---|---|---|---|
| 3,117,569 A | | 1/1964 | Wegner |
| 4,642,104 A | | 2/1987 | Sakamoto et al. |
| 5,004,454 A | | 4/1991 | Beyar et al. |
| 5,007,897 A | | 4/1991 | Kalb et al. |
| 5,082,006 A | | 1/1992 | Jonasson |
| 5,090,424 A | | 2/1992 | Simon et al. |
| 5,114,398 A | | 5/1992 | Trick et al. |
| 5,131,906 A | | 7/1992 | Chen |
| 5,140,999 A | | 8/1992 | Ardito |
| 5,306,226 A | | 4/1994 | Salama |
| 5,479,945 A | * | 1/1996 | Simon ........................ 128/885 |
| 5,554,147 A | | 9/1996 | Batich et al. |
| 5,607,417 A | | 3/1997 | Batich et al. |
| 5,624,395 A | * | 4/1997 | Mikhail et al. ................ 600/29 |
| 5,670,111 A | * | 9/1997 | Conway et al. .............. 264/264 |
| 5,671,755 A | * | 9/1997 | Simon et al. ................. 128/885 |
| 5,749,826 A | * | 5/1998 | Faulkner ........................ 600/29 |
| 5,788,687 A | | 8/1998 | Batich et al. |
| 5,806,527 A | * | 9/1998 | Borodulin et al. ........... 128/885 |
| 5,813,974 A | * | 9/1998 | Dolade Guardia ........... 600/29 |
| 5,887,593 A | * | 3/1999 | Levius ......................... 128/885 |
| 5,906,575 A | * | 5/1999 | Conway et al. ................ 600/29 |
| 5,910,316 A | | 6/1999 | Keefer et al. |
| 5,916,176 A | | 6/1999 | Caillouette |
| 5,954,688 A | | 9/1999 | Adams et al. |
| 5,954,869 A | | 9/1999 | Elfersy et al. |
| 5,959,014 A | | 9/1999 | Liebeskind et al. |
| 6,039,967 A | | 3/2000 | Ottoboni et al. |
| 6,070,588 A | * | 6/2000 | Pham .......................... 128/885 |
| 6,090,038 A | * | 7/2000 | Zunker et al. .................. 600/29 |
| 6,090,098 A | * | 7/2000 | Zunker et al. ............... 128/885 |
| 6,171,230 B1 | * | 1/2001 | Hakky et al. .................. 600/29 |

OTHER PUBLICATIONS

Thesis entitled "Design Of An Intra–Urethral Device for Incontinence" prepared by Elizabeth M. Burke (Dec., 1996).

* cited by examiner

Primary Examiner—Eric F. Winakur
Assistant Examiner—Nikita R Veniaminov
(74) Attorney, Agent, or Firm—Dority & Manning, P.A.

(57) ABSTRACT

An intraurethral device that can be used to inhibit leakage of urine due to incontinence is provided. The intraurethral device can include a urethral plug made from a biocompatible, flexible material. The intraurethral device can also include a first insertion element in operative communication with a second insertion element to facilitate self-insertion of the urethral plug into the urethra. Furthermore, in some instances, various mechanisms can be provided to keep the intraurethral device substantially sterile and/or clean prior to and/or during the insertion process.

41 Claims, 6 Drawing Sheets

FIG. 3A
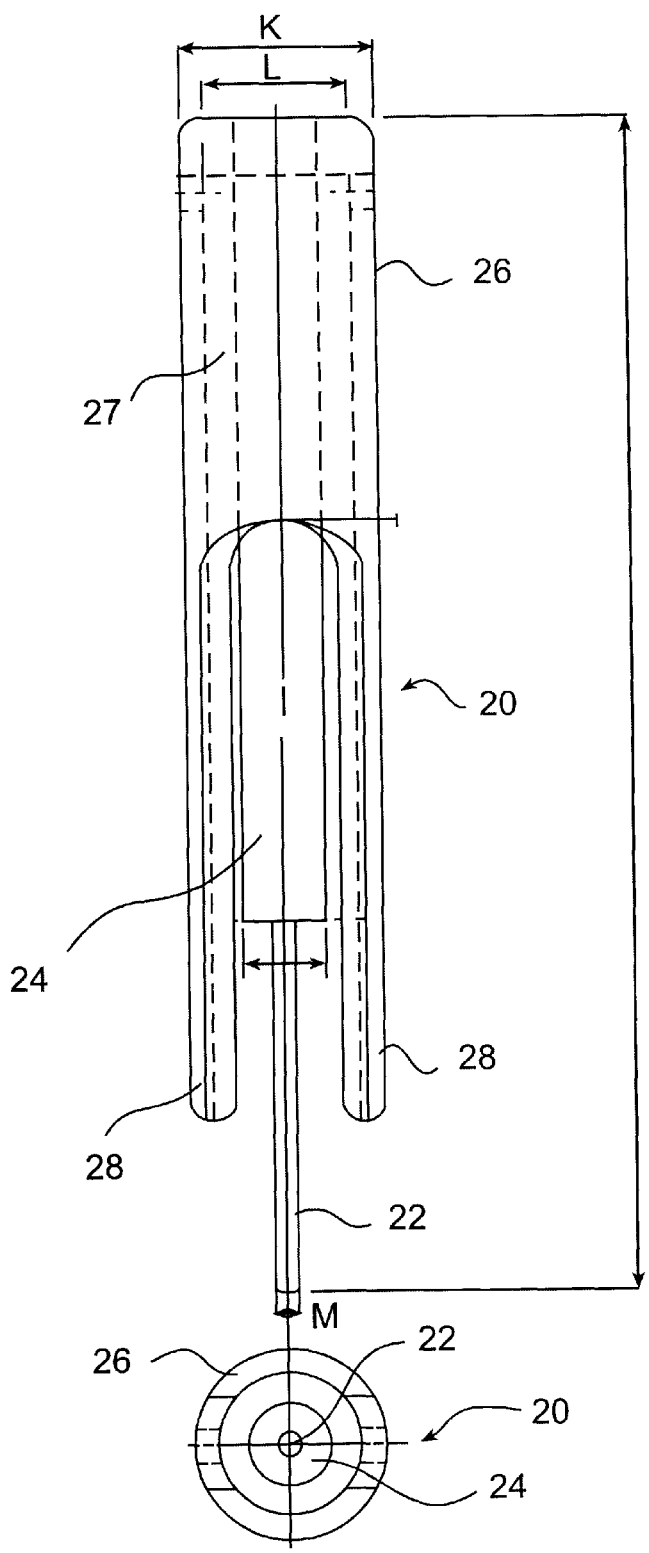
FIG. 3B
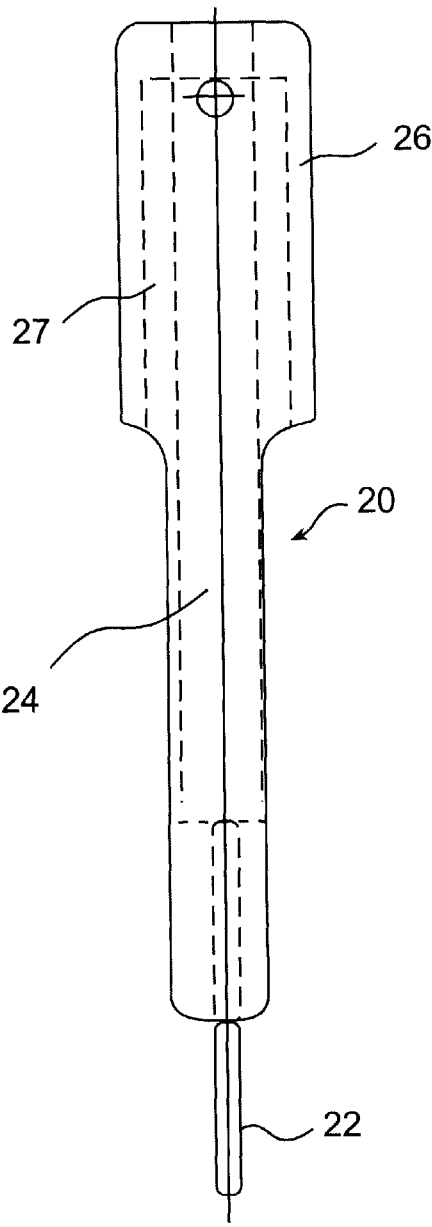
FIG. 3C

FIG. 6A  FIG. 6B

INTRAURETHRAL DEVICE FOR INCONTINENCE

BACKGROUND OF THE INVENTION

The urinary system generally works to ensure that a person can control micturition. As the bladder fills, muscles stretch and nerves signal the brain that the bladder is full, leading to the urge to urinate. In continent persons, a voluntary decision is then made whether or not to urinate. When it is desirable to not urinate, the spinal cord transmits the message from the brain telling the external sphincter to contract. As the external sphincter contracts, it signals the bladder to relax and the bladder neck to stay closed, and the urge to urinate subsides.

Additionally, the contraction of the sphincter increases the intraurethral pressure, such that it is greater than the intravesical pressure, thereby preventing urine passage through the urethra. This difference between the intravesical pressure and the intra-urethral pressure is termed the urethral closure pressure. When a person desires to void, the brain signals the external sphincter to relax, decreasing pressure in the urethra until urethral pressure is less than the intravesical (bladder) pressure and flow ensues.

Incontinence, or the inability to retain urine, can be broadly divided into five types. Stress incontinence results from an increase in intra-abdominal pressure, which is translated to the bladder, and for which the rhabdosphincter and pelvic floor muscles cannot compensate. Urge incontinence is a sudden need to urinate that is so urgent it cannot be controlled. This may be associated with spasm of the bladder muscle. Mixed incontinence patients experience both stress and urge incontinence. Overflow incontinence occurs when the bladder fails to empty completely due to obstruction. Small amounts of urine are lost because the bladder neck cannot remain closed against the full bladder. The last type of incontinence, functional incontinence, results when mobility limitations prevent the patient from getting to the bathroom; this is often compounded by spinal and/or nerve injury.

There are currently many prosthetic devices available to compensate for incontinence. Many of the devices, however, cause urinary tract infections. Some tend to slip or migrate during use and end up in the bladder, where they may cause a great deal of harm and require invasive surgical procedures for removal. Other devices are permanent devices, which require surgery for implementation and have long-term biocompatibility problems.

For instance, U.S. Pat. No. 5,131,906 to Chen describes a device including a centrally disposed rod or tube member, a truncated spherical shell extending from one end of the member, and a plurality of elastic bands uniformly spaced around the shell periphery. Moreover, U.S. Pat. No. 5,090,424 to Simon et al. describes a flexible urethral plug including a soft inflatable plastic catheter and a transportable fluid which is moved from an external bellows to inflate the catheter within the urethra to block urine flow. Another example of such a device is disclosed in U.S. Pat. No. 5,306,226 to Salama. Salama relates to a urine tube extending through a balloon that is inflated in the neck of the bladder to seal the urethra.

However, all of the above devices suffer from common disadvantages, including a susceptibility to urine encrustation and provision for direct entry of bacteria into the bladder. Additionally, the spherical design of the aforementioned devices may not totally prevent urine leakage. Because of the fluid mechanics inherent with the spherical design, backpressure caused by urine in the bladder may compress a spherical device, while simultaneously causing the urethral walls to expand, allowing urine to leak.

Other prior art incontinence control devices include devices permanently installed within the urethra, such as those disclosed in U.S. Pat. No. 5,114,398 to Trick et al.; U.S. Pat. No. 5,004,454 to Beyar et al.; and U.S. Pat. No. 5,140,999 to Ardito. However, these devices also suffer from some significant disadvantages including the requirement for surgical implantation, inclusion of metal parts subject to corrosion by urine, and need for patient manipulation to permit urination, which may introduce bacteria into the urethra.

Furthermore, temporary incontinence plugs have been previously described by U.S. Pat. No. 5,082,006 to Jonasson and by Nielson et al., "The Urethral Plug: A New Treatment Modality for Genuine Urinary Stress Incontinence in Women," *Journal of Urology* 144: 1199-1202 (1990). The Jonasson device describes an oblong shaft having at least one knob arranged at a distance from the proximal end of the shaft. This device permits undesirable leakage. Additionally, the device also allows bacteria to enter the urethra. The device described by Nielson et al. includes a tubular shaft having at least one 7 mm sphere located along the shaft. This device, however, may slip during use, allowing the device to migrate into the bladder and require surgical removal. Additionally, this device has no sealing mechanism to prevent urine outflow.

In response to the need for a sealing mechanism, a urethral plug, as described in a Master's thesis entitled "Design of an Intra-Urethral Device for Incontinence," by Elizabeth M. Burke (Clemson University Department of Bioengineering, December 1996), was developed to better inhibit urine leakage. In particular, a plug can be positioned in a urethra such that the open end of the plug faces bladder lumen, allowing urine to enter the hollow cavity of the plug. The pressure exerted by urine within the hollow cavity against the plug's sidewalls causes the sidewalls to outwardly flex in a radial direction and form a seal at the urethral wall.

Nevertheless, while these devices have attempted to address the problem of incontinence, none have been totally successful. As such, a need still exists for a temporary intraurethral device to that is easily insertable by the patient in a sterile manner. A need also exists for a temporary intraurethral device that can substantially inhibit urine leakage when desired and be voluntarily expelled.

SUMMARY OF THE INVENTION

In accordance with one embodiment of the present invention, an intraurethral device is provided for use in a female urinary tract. In particular, the intraurethral device contains a urethral plug, a first insertion element, and a second insertion element.

The urethral plug has a distal end and a proximal end. The proximal end defines a plug opening and the distal end is adapted to be inserted into a urethra. For example, in one embodiment, the proximal end of the urethral plug includes a flange for inhibiting over-insertion of the urethral plug into said urethra. Moreover, the distal end has a shape that enables the urethral plug to form a seal with the urethra when inserted therein to substantially inhibit urine leakage from the urethra around the urethral plug. For instance, in one embodiment, the distal end has a shape that forms a generally concave surface, such as a cup-shape.

The first insertion element has an inner surface and an outer surface and at least a portion of the first insertion element is configured to be removably inserted through the plug opening. For example, in one embodiment, the first insertion element contains an elongated element that is configured to be removably inserted through the plug opening defined by the proximal end. In some instances, the first insertion element can also contain an inner body portion having a first end and a second end. For example, the first end of the inner body portion can be connected to the elongated element. Moreover, the second end of the inner body portion can be connected to an outer body portion of the first insertion element.

The second insertion element has an inner surface and an outer surface. The second insertion element defines a channel through which the proximal end of the urethral plug can be inserted. For example, in one embodiment, as stated above, the proximal end of the plug can include a flange that can be inserted through the channel of the second insertion element.

The first insertion and second insertion elements can provide a number of benefits to the intraurethral device. For instance, in many instances, the second insertion element can at least partially surround the urethral plug so that the plug does not come into contact with substantial amounts of bacteria, fungi, or other microorganisms prior to being inserted into a urethra. In addition, the first and second insertion elements can also be placed into operative communication to help in the insertion of the urethral plug into a urethra. For instance, in one embodiment, the inner surface of the second insertion element is placed adjacent to the outer surface of the first insertion element such that the second insertion element is in operative communication with the first insertion element.

In some embodiments, the intraurethral device can also contain additional mechanisms for enhancing the ability of the urethral plug to remain clean and/or sterile prior to and/or during insertion. For example, in one embodiment, an enclosure can be provided that surrounds at least a portion of the urethral plug so that the enclosure is capable of substantially maintaining the cleanliness and/or sterility of the urethral plug before being inserted into the urethra. In one embodiment, the enclosure is attached to the second insertion element.

In accordance with another embodiment of the present invention, a method of substantially inhibiting the leakage of urine from a female urinary tract is provided. Specifically, an intraurethral device, such as described above, is first provided. The urethral plug of the intraurethral device is aligned with the urethra and the urethral plug is inserted therein by moving the first insertion element in a direction towards the urethra and thereafter moving the second insertion element in a direction away from the urethra to substantially release the flange from the second insertion element. For example, in one embodiment, the flange of the urethral plug is initially provided in a rolled-up, U-shape within the second insertion element. By moving the second insertion element away from the urethra, the U-shaped flange can be unrolled into a flat position to inhibit over-insertion of the urethral plug.

Once the urethral plug is inserted, the first insertion element is removed from the plug opening. Due to the shape of the distal end of the urethral plug, a seal can be formed between the urethral plug and the urethra to substantially inhibit urine leakage from the urethra around the urethral plug.

Other features and aspects of the present invention are discussed in greater detail below.

BRIEF DESCRIPTION OF THE DRAWINGS

FIG. 2 illustrates one embodiment of the present invention, in which

FIG. 3 illustrates the outer insertion element of one embodiment of an intraurethral device of the present invention, in which FIG. 3A is a front view of the outer insertion element, FIG. 3B is a side view of the outer insertion element; and FIG. 3C is a bottom view of the outer insertion element;

FIG. 4 illustrates the inner insertion element of one embodiment of an intraurethral device of the present invention, in which

FIG. 5 illustrates one embodiment of an intraurethral device of the present invention, in which FIG. 6 illustrates the urethral plug of one embodiment of an intraurethral device of the present invention, in which FIG. 6A is a front view of the urethral plug, FIG. 6B is a side view of the urethral plug.

Figure 1:
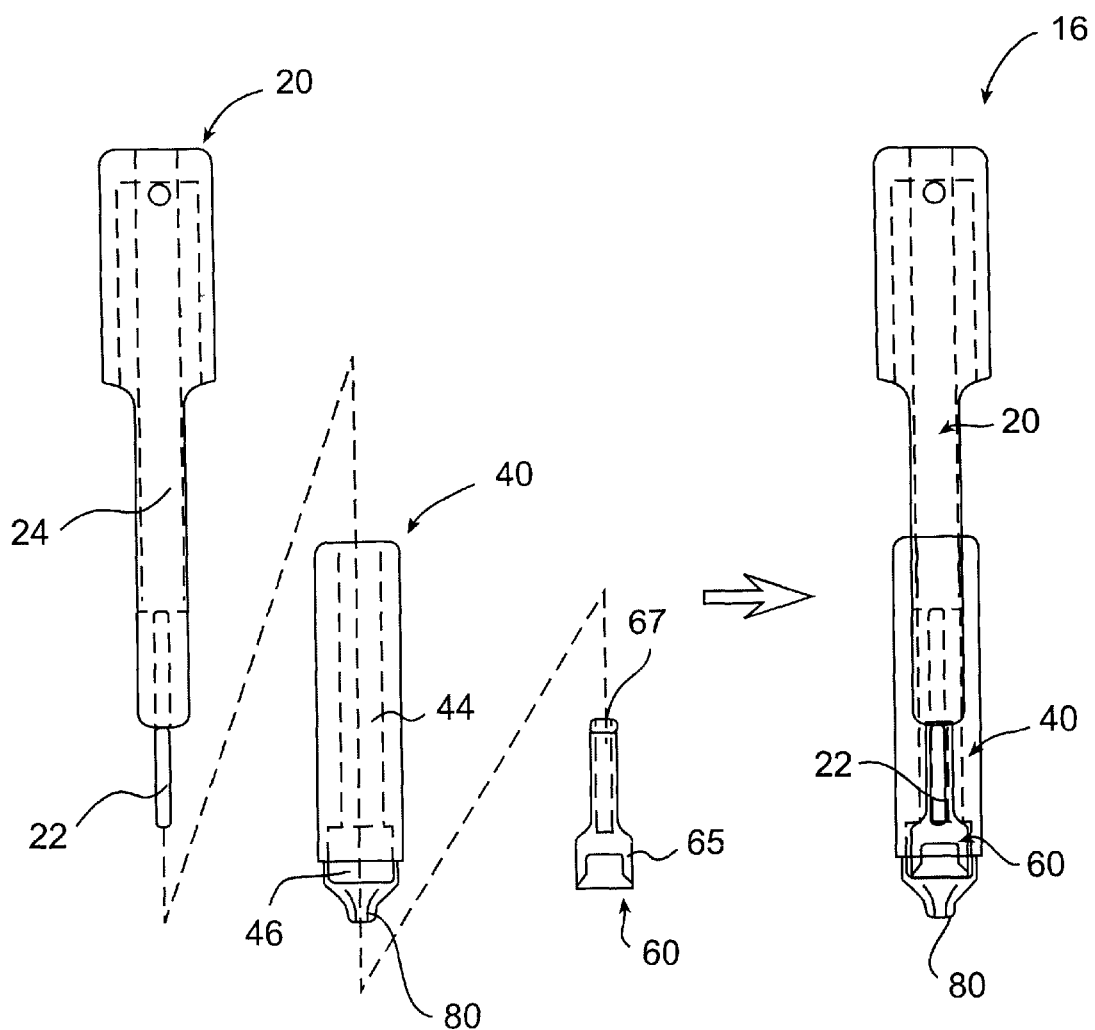
FIG. 1 illustrates one embodiment of an intraurethral device of the present invention.

Repeat use of reference characters in the present specification and drawings are intended to represent same or analogous features or elements.

DETAILED DESCRIPTION OF THE REPRESENTATIVE EMBODIMENTS

It is to be understood by one of ordinary skill in the art that the present discussion is a description of exemplary embodiments only, and is not intended as limiting the broader aspects of the present invention, which broader aspects are embodied in the exemplary construction.

The present invention is generally directed to a disposable intraurethral device and method for treating urinary incontinence in females on a short-term basis. Specifically, an intraurethral device of the present invention can be easily inserted into a urethra in a clean and/or sterile manner in order to inhibit urine leakage.

Referring to FIG. 1, for example, one embodiment of an assembled intraurethral device 10 is illustrated. As shown, the intraurethral device 10 includes an outer insertion element 20, an inner insertion element 40, and a urethral plug 60.

Figure 6C:
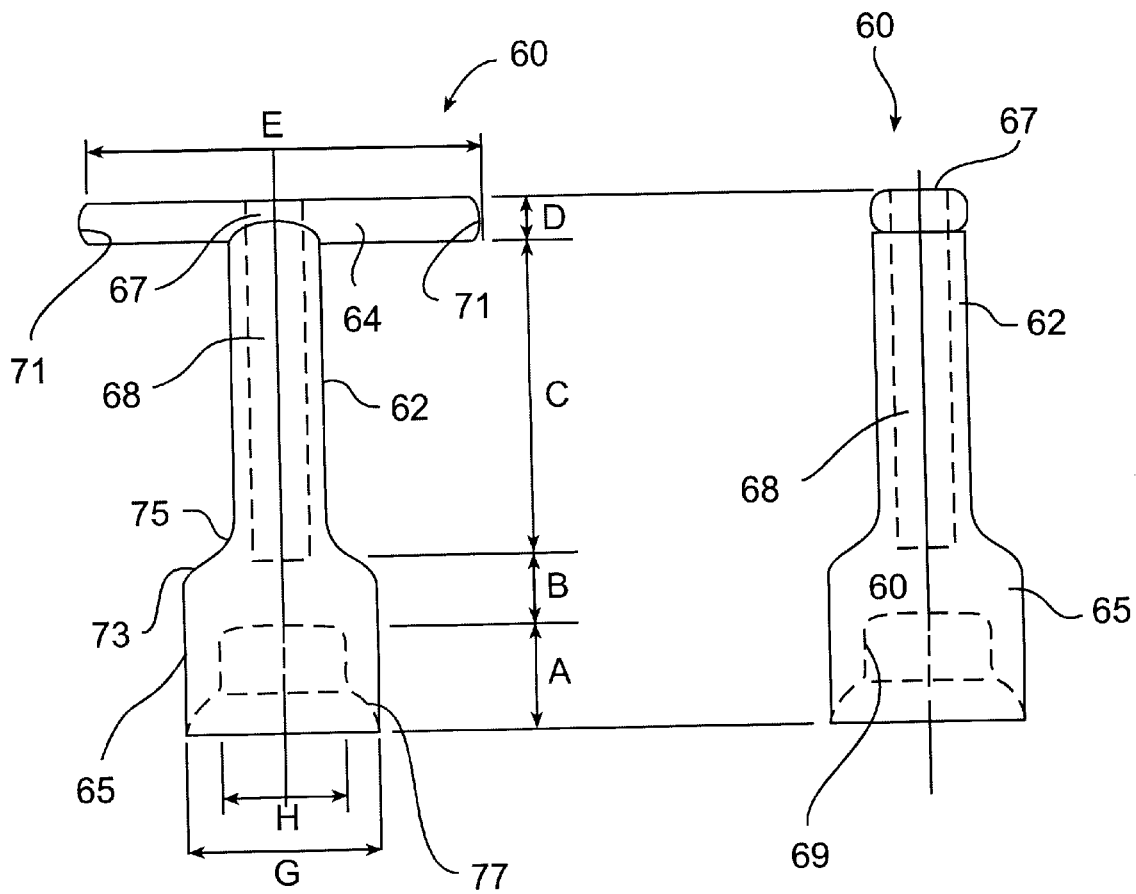
FIG. 6C is a top view of the urethral plug.
Figure 6C:
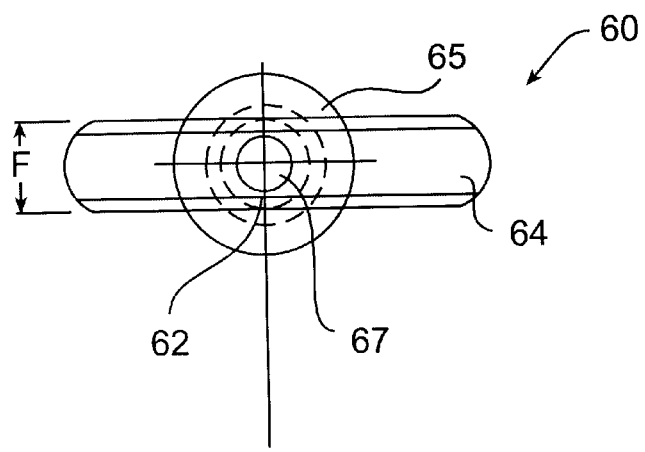

The urethral plug 60 can generally be any well-known design of a urethral plug that can be inserted into a patient's urethra. For example, one embodiment of a flexible urethral plug 60 that can be utilized in the present invention is depicted in FIGS. 6A–6C. As shown, the urethral plug 60 includes a distal end 65 connected to a proximal end 64 by a tubular section 62. Specifically, in this embodiment, the proximal end 64 is an external flange that is capable of substantially preventing over-insertion of the plug 60 and/or to aid in the removal of the plug 60. Moreover, the distal end 65 has a cup-shape that forms a generally concave surface 69. It should be understood, however, that the present invention is not limited to a cup-shaped urethral plug and that any other shape capable of providing a generally concave surface can also be utilized. Further, it should also be understood that a generally concave surface is not required in all embodiments of the present invention.

In general, the urethral plug 60 can be made in a variety of ways. Typically, the urethral plug 60 can be made from a material that is generally biocompatible such that it is suitable for contact with the urethra. In some embodiments, the urethral plug 60 can be made from a biocompatible material that is also flexible. Although not required, flexible materials can sometimes allow the urethral plug 60 to form a better seal with the walls of the urethra. For instance, some examples of suitable flexible materials can include, but are not limited to, elastomeric polymers, such as polyurethane, silicone rubber, natural rubber, polyester, chloroprene, polybutadiene, combinations thereof, or any other elastomeric material suitable for urethral and urine contact. One particular example of an elastomer suitable for use in making the plug 60 is silicone rubber, such as medical grade silicone rubber commonly used in various medical devices. However, it should be understood that any other elastomeric material can be used in the present invention.

Moreover, the urethral plug 60 need not be made from the same material(s). For example, the cup-shaped end 65, the tubular section 62, and the external flange 64 may all contain different material(s), if desired. In one embodiment, for instance, the cup-shaped end 65 can be made from a flexible elastomeric material, while the external flange 64 and the tubular section 62 can conversely be made from a less flexible or non-flexible material.

The component(s) of the urethral plug 60 can also generally possess any desired dimension or shape. In general, a physician usually determines the precise size for use, after measuring the patient's urethra. In particular, a urethral plug 60 can be made into a variety of different shapes and sizes to better conform to different urethras. Moreover, in some embodiments, because the plug 60 can also conform to the size and shape of the urethra after insertion, there may be no need to custom make the plug.

For example, in one embodiment, as shown in FIGS. 6A–6B, the plug 60 can have a total length of between about 15 millimeters ("mm") to about 30 mm in length, and in one particular embodiment, the length can be about 25 mm. In particular, as shown, the total length of the urethral plug 60 is approximately equal to the combined values of the dimensions represented as "a", "b", "c", and "d". These dimensions can generally be selected to have any value, depending on the desired shape and size of the urethral plug. For example, in one embodiment, the dimensions represented as "a", "b", "c", and "d" are 5.0 mm, 3.0 mm, 15 mm, and 2 mm, respectively.

Besides having a certain length, the component(s) of the urethral plug 60 can also have other varying dimensions. For example, in some embodiments, the outer diameter of the tubular section 62 can be between about 2 mm to about 8 mm, and in one particular embodiment, about 4.0 mm. Further, in some instances, the tubular section 62 can define a hollow channel 68 that extends through the flange 64 to form a plug opening 67. Thus, in this embodiment, the inner diameter of the tubular section 62 can be between about 1 mm to about 7 mm, and in one particular embodiment, about 2.5 mm.

In addition, the width dimension "e" of the flange 64 can be between about 10 mm to about 40 mm, and in one particular embodiment, about 18 mm. Moreover, the thickness dimension "f" of the flange 64 can be between about 2 mm to about 8 mm, and in one particular embodiment, about 4.0 mm. The outer edges 71 of the flange 64 can also be rounded, such as having a radius of curvature of about 2.0 mm.

Further, the cup-shaped end 65 can also possess a variety of different dimensions. For example, in the illustrated embodiment, the cup-shaped end 65 has an outer diameter "g" of between about 4 mm to about 16 mm, and in one particular embodiment, about 8.0 mm. Moreover, the cup-shaped end 65 also has an inner diameter "h" of between about 3 mm to about 15 mm, and in one particular embodiment, about 5.0 mm. In addition, as shown, the cup-shaped end 65 can contain one or more rounded surfaces to better inhibit urinary leakage. For example, in one embodiment, as shown in FIG. 6A, the cup-shaped end 65 contains a rounded surface 77, which has a radius of curvature of about 5.0 mm.

In some embodiments, the urethral plug 60 can also have a one or more rounded surfaces to minimize tissue irritation when inserted into the urethra. For example, as shown, the urethral plug 60 can contain rounded surfaces 73 and 75 to reduce tissue irritation. In one embodiment, the rounded surfaces can have a radius of curvature of about 2.5 mm and about 4.0 mm, respectively.

In general, the size of urethral plug 60 in relation to the urethra may be such that plug 60 can inhibit urine leakage without external pressure being applied by the periurethral muscle, until urine back pressure reaches approximately 0.3–0.4 psi. At approximately 0.3–0.4 psi, the plug 60 can release from its intraurethral position and move towards the external urethral meatus. However, in some embodiments, application of as little as 0.1 psi pressure by the surrounding periurethral muscle can significantly increase the "holding power" of the urethral plug 60. When the patient voluntarily releases external pressure applied to urethral plug 60 by the periurethral muscle, the urethra can shorten and dilate, causing the urethral plug 60 to be released from the urethra and facilitating urination.

Referring again to FIG. 1, the intraurethral device 10 also contains an outer insertion element 20 and an inner insertion element 40. Specifically, as described in more detail below, the inner insertion element 40 can help maintain the sterility and/or cleanliness of the urethral plug 60 prior to its insertion into a urethra. Furthermore, the inner insertion element 40 can be used in conjunction with the outer insertion element 20 to facilitate the insertion of the urethral plug 60 into the urethra.

For example, referring to FIGS. 3A–3C, one embodiment of an outer insertion element 20 that can be used in the present invention is illustrated. As shown, the outer insertion element contains an inner body portion 24 that is attached at one end to an outer body portion 26. In addition, the outer insertion element 20 also contains an elongated element 22 (e.g., shaft) that is attached at one end to the inner body portion 24. In general, any of a variety of attachment mechanisms, such as adhesives, can be utilized in attaching the portions of the outer insertion element 20. Moreover, instead of being formed from multiple portions, the outer insertion element 20 can also be formed as one integral portion.

The portion(s) of the outer insertion element 20 can be formed to have a variety of different shapes and/or sizes. For example, in one embodiment, as shown in FIGS. 3A–3C, the elongated element 22, the inner body portion 24, and the outer body portion 26 have a cylindrical, tube-like shape.

These portions may be solid or define a hollow channel. For example, in the illustrated embodiment, the outer body portion 26 defines a cylindrical, tube-like channel 27 for placement of the inner body portion 24 therein.

When having a cylindrical shape, the diameter of the elongated element 22, the inner body portion 24, and the outer body portion 26 can generally vary. For instance, in one embodiment, the outer diameter "i" of the inner body portion 24 can be about 6.9 mm, the outer diameter "k" of the outer body portion 26 can be about 16.0 mm, the inner diameter "l" of the outer body portion 26 can be about 12.1 mm, and the outer diameter "m" of the shaft 22 can be about 2.0 mm.

Besides having a certain diameter (or width), the length of one or more portions of the outer insertion element 20 can also be selectively varied as desired. In one embodiment, for instance, the length "n" of the entire insertion element 20 can be about 100 mm. Specifically, in the illustrated embodiment, the length of the elongated element 22 is about 32 mm and the length of the inner body portion 24 is about 68 mm. Further, in one embodiment, the length of the outer body portion 26 (including the flanges 28) can be about 86.0 mm and the length of the hollow channel 27 defined by the outer body portion 26 can be about 35.0 mm.

In accordance with one embodiment of the intraurethral device of the present invention, an additional inner insertion element 40 is utilized in operative communication with the outer insertion element 20 to facilitate insertion of the urethral plug 60 into a urethra. Moreover, the inner insertion element 40 can also help to maintain the sterility and/or cleanliness of the urethral plug 60 prior to its insertion into a urethra.

Figure 4A:
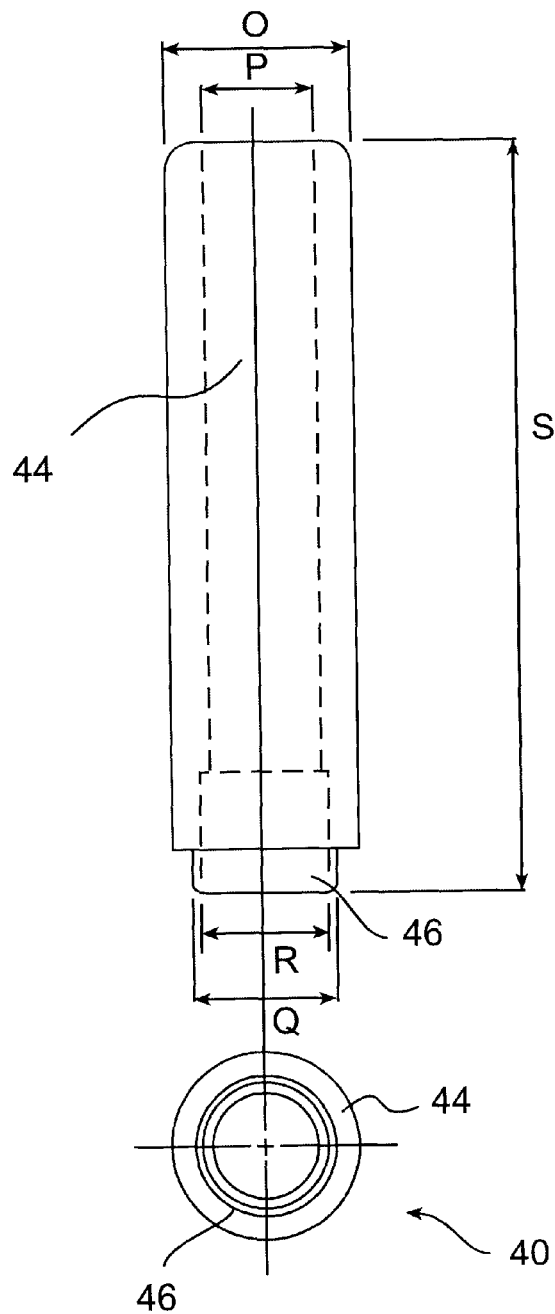
FIG. 4A is a front view of the inner insertion element.
Figure 4B:
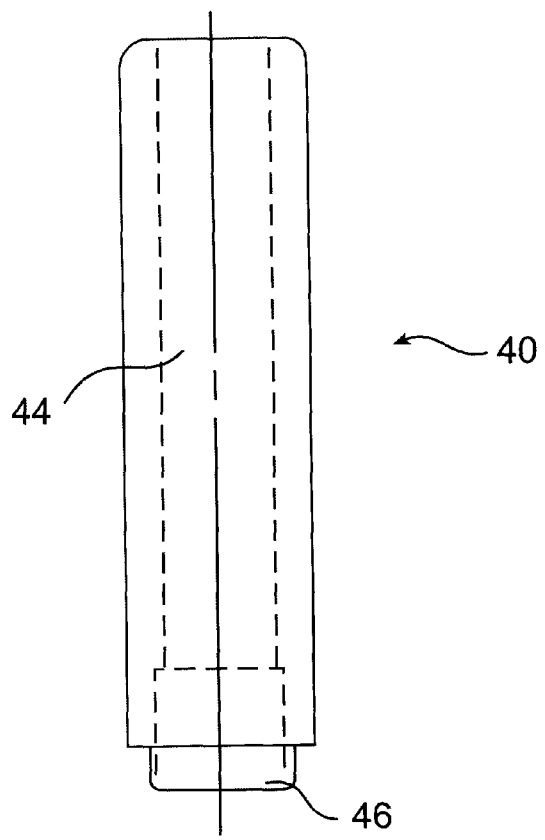
FIG. 4B is a side view of the inner insertion element.
Figure 4C:
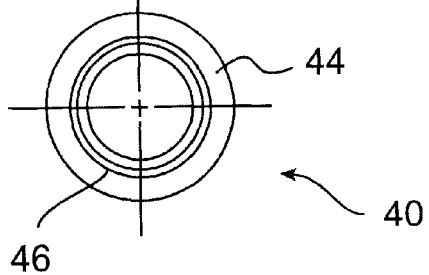
FIG. 4C is a bottom view of the inner insertion element.

For example, referring to FIGS. 4A–4C, one embodiment of an inner insertion element 40 that can be used in the present invention is illustrated. As shown, the inner insertion element 40 contains a first body portion 44 attached to a second body portion 46. Specifically, in this embodiment, the outer cylindrical surface of the second body portion 46 is attached to the inner cylindrical surface of the first body portion 46. In general, any of a variety of attachment mechanisms (e.g., adhesives, etc.) can be utilized to attach the portions 44 and 46 of the inner insertion element 40. Moreover, instead of being formed from multiple portions, the inner insertion element 40 can also be formed as one integral portion.

The portion(s) of the inner insertion element 40 can generally be formed to have a variety of different shapes and/or sizes. For example, in one embodiment, as shown in FIGS. 4A–4C, the first body portion 44 and the second body portion 46 have a cylindrical, tube-like shape. Moreover, in the illustrated embodiment, both the first and second body portions 44 and 46 define cylindrical, tube-like channels for placement of the inner insertion element 20 therein, as will be described in more detail below.

When having a cylindrical shape, the diameter of the first body portion 44 and the second body portion 46 can generally vary. In one embodiment, for instance, the outer diameter "o" of the first body portion 44 can be about 12.0 mm, the inner diameter "p" of the first body portion 44 can be about 7.0 mm, the outer diameter "q" of the second body portion 46 can be about 9.1 mm, and the inner diameter "r" of the second body portion 46 can be about 8.1 mm.

Besides having a certain diameter (or width), the length of one or more portions of the inner insertion element 40 can also be selectively varied as desired. In one embodiment, for instance, the length "s" of the entire insertion element 40 can be about 50 mm. In particular, in the illustrated embodiment, the length of the first body portion 44 is about 47 mm, the length of the second body portion 46 is about 8 mm, and the portion 46 extends beyond the portion 44 by approximately 3 mm.

In general, the portion(s) of the insertion elements 20 and 40 can be made any of a variety of materials, such as rigid and/or semi-rigid materials. In some embodiments, for instance, the insertion elements 20 and 40 can contain plastic materials, such as polyolefins, polyamides, polycarbonates, etc; paper materials, such as cardboard; and the like. Moreover, in another embodiment, the insertion elements 20 and 40 can contain a semi-rigid rubber material, such as polyurethane. It should be understood, however, that the insertion elements 20 and 40 need not be made from the same material. Moreover, the components of a single insertion element can also be made from different materials if desired.

Figure 5A:
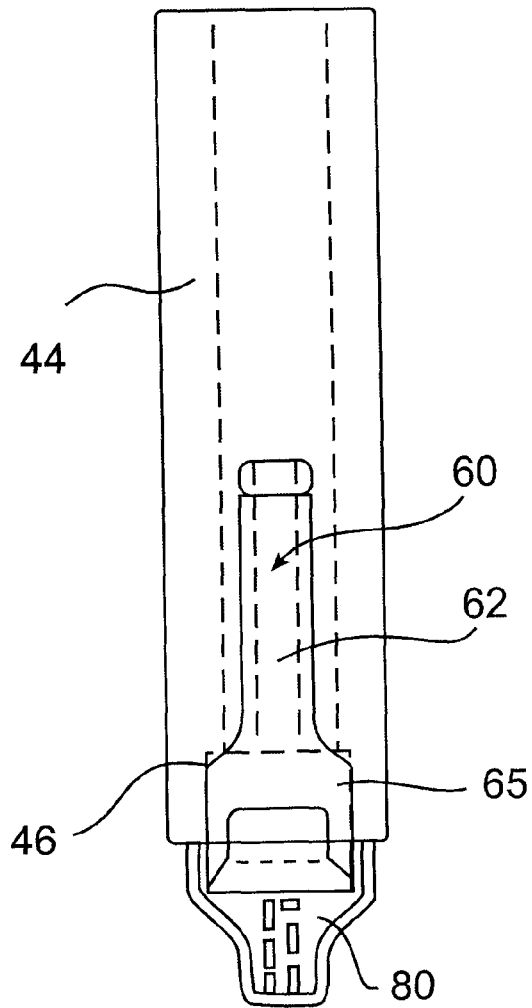
FIG. 5A shows a roll-out nipple in its rolled-up position and FIG. 5B shows the roll-out nipple in its unraveled position.
Figure 5B:
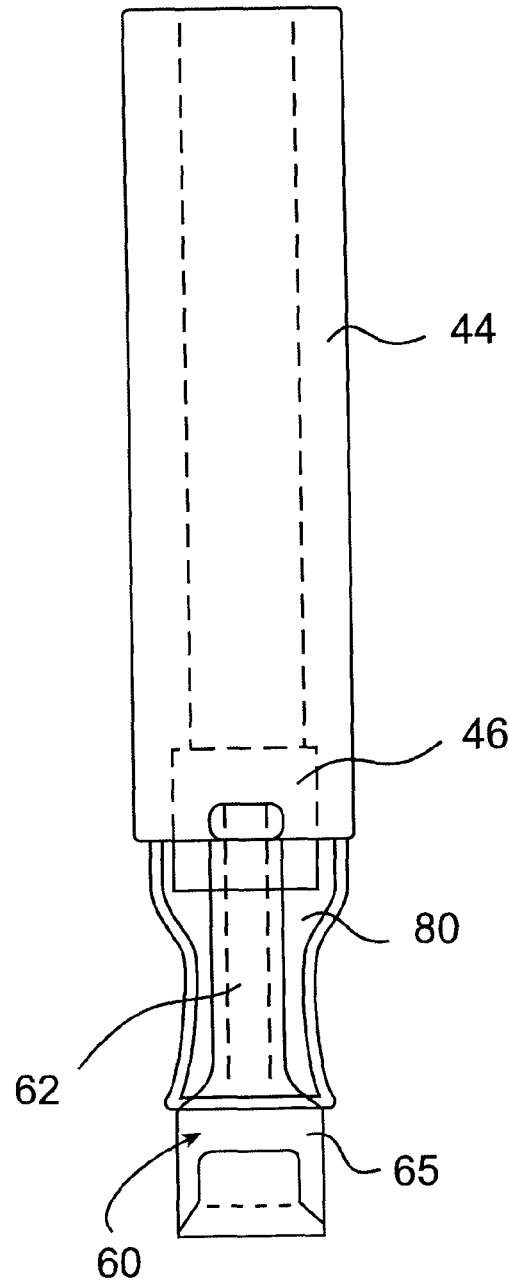

In some embodiments, besides the inner insertion element 40, the intraurethral device 10 can also be provided with other mechanisms for enhancing the ability of the urethral plug 60 to remain sterile and/or clean. For example, as shown in FIGS. 5A–5B, an enclosure, such as a roll-out nipple 80, can be attached to the second body portion 46 of the inner insertion element 40 in such a manner that the nipple 80 substantially covers the plug 60 prior to its insertion in a urethra. The nipple 80 can be made from any of a variety of materials, such as various plastics or rubber materials. Moreover, the nipple 80 can also be sealed to the inner insertion element 40 according to any sealing method known in the art. If desired, still other devices can be utilized to enhance the ability of the urethral plug 60 to remain relatively sterile prior to and/or during insertion.

For example, in one embodiment, some or all of the intraurethral device 10 can be enclosed with an additional sterile bag (not shown). If desired, certain adhesives (e.g., starch) may also be utilized to ensure that the nipple 80 remains enclosed at its tip prior to use of the intraurethral device.

In one embodiment, the components described above can be assembled to form the intraurethral device according to the process illustrated in FIG. 1. Such assembly can be performed by a user, a medical professional, or during manufacture of the device. For instance, referring to FIG. 1, the inner insertion element 40 can initially be placed into operative communication with the outer insertion element 20 by positioning the inner cylindrical surface of the first body portion 44 over the outer cylindrical surface of the inner body portion 24 such that the inner insertion element 40 fits between the flanges 28 of the outer insertion element 20. (See FIGS. 3A–3C). As a result, the inner insertion element 40 can slide along the entire length of the inner body portion 24.

Thereafter, the inner insertion element 40 is moved along the length of the inner body portion 24 of the outer insertion element 20 such that at least a portion of the elongated element 22 extends beyond the inner insertion element 40. Once positioned in this manner, the plug opening 67 of the urethral plug 60 is then placed over the portion of the elongated element 22 that extends beyond the inner insertion element 40. However, it should be understood that the urethral plug 60 can generally be connected to the elongated element 22 utilizing any desired method.

Figures 2A, 2B, 2C, 2D:
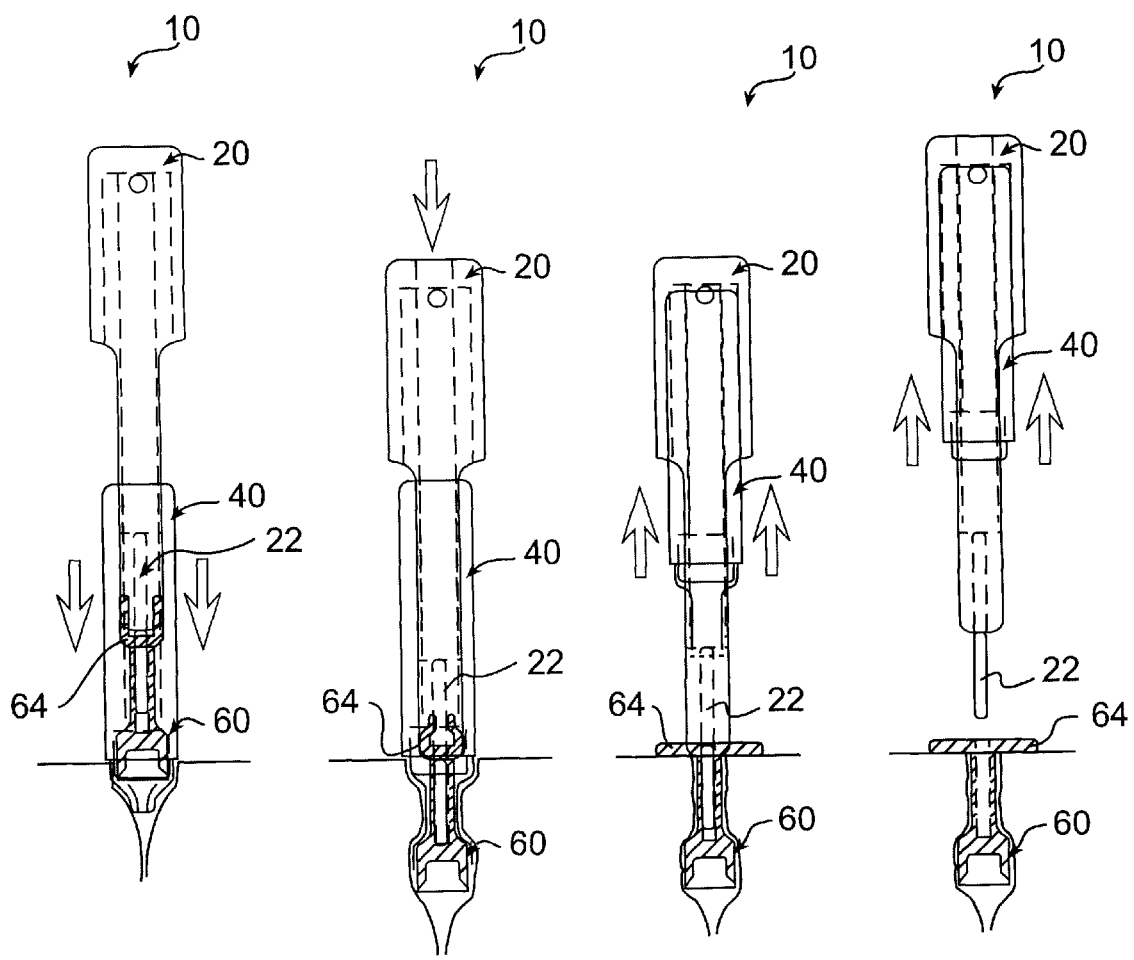
FIG. 2A shows the alignment of the intraurethral device with a urethra.
FIG. 2B shows the initial insertion of the urethral plug into the urethra.
FIG. 2C shows the partial withdrawal of the second insertion element of the urethral plug.
FIG. 2D shows the complete withdrawal of both of the insertion elements.

Once the urethral plug 60 is positioned on the elongated element 22, the inner insertion element 40 is then moved in the direction of the urethral plug 60 while the outer insertion element 20 is held in place or moved away from the urethral plug 60. Upon contacting the inner insertion element 40, the flange 64 folds into a U-shape, such as shown in FIG. 2A. Due to the friction between the surface of the flexible flange 64 and the inner surface of the inner insertion element 40, the flange 64 remains in its folded state. The inner insertion element 40 containing the folded flange 64 is further moved until the second body portion 46 is placed in contact with the cup-shaped end 65 of the urethral plug 60. At this point, the intraurethral device 10 is assembled and ready for use.

Referring to FIGS. 2A–2D, one method for inserting the urethral plug 60 of the intraurethral device 10 shown in FIG. 1 into a urethra is illustrated. In particular, as shown in FIG. 2A, a user or medical professional grasps the intraurethral device in an outwardly extended position and aligns the roll-out nipple 80 and urethral plug 60 with a urethra opening. Once properly positioned, the outer insertion element 20 is moved toward the urethra, as indicated by the directional arrow of FIG. 2B. In some instances, it may be desired to simultaneously hold the inner insertion element 40 in place while the outer insertion element 20 is moved toward the urethra. The downward motion of the outer insertion element 20 causes the elongated element 22 and the urethral plug 60 to be inserted into the urethra. In addition, as shown in FIGS. 2B and 5A–5B, the downward motion of the outer insertion element 20 causes the roll-out nipple 80 to unravel, such that the urethral plug 60 does not generally come into contact with a non-sterile surface, and thus, does not drag substantial amounts of bacteria, fungi, or other pathogenic microorganisms into the urethra, prior to and/or during insertion.

In one embodiment, as shown in FIG. 3A, the outer body portion 26 contains two flanges 28. Thus, as the outer insertion element 20 is moved towards the urethra, the flanges 28 come into contact with the urethra wall, thereby inhibiting any further downward movement of the outer insertion element 20. In this manner, over-insertion of the urethral plug can be substantially prevented.

Once the urethral plug 60 is positioned within the urethra, the inner insertion element 40 is then moved upward, as indicated by the directional arrow shown in FIG. 2C. In some instances, it may also be desired to simultaneously hold the outer insertion element 20 in place while moving the inner insertion element 40 away from the urethra. The upward motion of the inner insertion element 40 causes the urethral plug 60 to be released from the elongated element 22, thereby unrolling the flange 64 of the urethral plug 60 from its U-shaped position into a flat position, such as shown in FIG. 2C. Because the unrolled flange 64 has a width greater than the width of the urethra opening, it can inhibit over-insertion of the urethral plug 60 therein.

After inserting the urethral plug 60, the insertion elements 20 and 40 can then be completely removed. For example, as depicted in FIG. 2D, a user can withdraw the elongated element 22 by pulling the insertion element 20 in an outwardly direction, as indicated by the directional arrow depicted in FIG. 2D.

The urethra plug 60, which is now positioned within the urethra, can substantially inhibit urine leakage around the plug 60. For example, in the embodiment described above, the generally concave surface of the cup-shaped end 65 of the urethral plug 60 can face the bladder and form an effective seal against involuntary leakage. In particular, the fluid pressure from the bladder and the rhabdosphincter pressure can hold the urethral plug 60 against the intraurethral walls, thus forming a seal around the plug 60 to inhibit urine leakage. If desired, the outside of the urethral plug 60 can also be also coated with a lubricant, such as VASELINE or K-Y JELLY, prior to insertion into the urethra in order to assist in seal formation and to protect sensitive urethral tissue.

In general, the urethral plug 60 can be removed in a variety of ways. In most instances, the urethral plug 60 can be removed without the aid of a medical professional. In particular, removal can normally be accomplished manually or by voluntary urinary exertion. Moreover, although not necessary, a variety of other mechanisms can also be utilized to facilitate the removal of the urethral plug 60. For instance, in some embodiments, the urethral plug 60 can include a removal device (not shown), such as a string, filament, cord, tether, and the like, to facilitate manual removal of the plug 60. A removal device can generally allow the patient to facilitate manual plug removal as desired, by manually exerting pressure on the device. Additionally, should expulsion not occur when the plug 60 is released from its intraurethral location, a removal device can also allow the patient to completely remove the plug 60. It should be understood that a removal device may be secured to the plug 60 by any suitable method known in the art, as long as adequate strength is present to facilitate manual removal of the plug by applying a force to the removal device. For example, in one embodiment, the removal device may be molded as a unitary structure with the urethral plug 60.

These and other modifications and variations of the present invention may be practiced by those of ordinary skill in the art, without departing from the spirit and scope of the present invention, which is set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed is:

1. An intraurethral device for use in a female urinary tract comprising:
    a urethral plug having a distal end and a proximal end, said proximal end defining a plug opening, said distal end being adapted to be inserted into a urethra, said distal end having a shape that enables said urethral plug to form a seal with the urethra when inserted therein to substantially inhibit urine leakage from the urethra around said urethral plug;
    a first insertion element having an inner surface and an outer surface, wherein at least a portion of said first insertion element is configured to be removably inserted through said plug opening;
    a second insertion element having an inner surface and an outer surface, said second insertion element defining a channel through which said proximal end of said urethral plug is capable of being inserted; and
    wherein said inner surface of said second insertion element is placed adjacent to said outer surface of said first insertion element such that said second insertion element is in operative communication with said first insertion element.

2. An intraurethral device as defined in claim 1, wherein said urethral plug contains a biocompatible material.

3. An intraurethral device as defined in claim 1, wherein said urethral plug contains an elastomeric material.

4. An intraurethral device as defined in claim 1, wherein the proximal end of said urethral plug includes a flange for inhibiting over-insertion of said urethral plug into said urethra.

5. An intraurethral device as defined in claim 4, wherein said flange is capable of being inserted into said channel of said second insertion element.

6. An intraurethral device as defined in claim 1, wherein the shape of said distal end forms a generally concave surface.

7. An intraurethral device as defined in claim 1, further comprising an enclosure that surrounds at least a portion of said urethral plug so that said enclosure is capable of substantially maintaining the sterility of said urethral plug before being inserted into the urethra.

8. An intraurethral device as defined in claim 7, wherein said enclosure comprises a roll-out nipple.

9. An intraurethral device as defined in claim 7, wherein said enclosure is attached to said second insertion element.

10. An intraurethral device as defined in claim 1, wherein said urethral plug further comprises a section having a tubular shape that connects said distal end and said proximal end of said urethral plug.

11. An intraurethral device as defined in claim 1, wherein said first insertion element contains an elongated element that is configured to be removably inserted through said plug opening.

12. An intraurethral device as defined in claim 11, wherein said first insertion element further contains an inner body portion having a first end and a second end.

13. An intraurethral device as defined in claim 12, wherein said first end of said inner body portion is connected to said elongated element.

14. An intraurethral device as defined in claim 12, wherein said first insertion element further contains an outer body portion, wherein said second end of said inner body portion is connected to said outer body portion.

15. An intraurethral device as defined in claim 14, wherein said outer body portion and said inner body portion have a cylindrical shape.

16. An intraurethral device as defined in claim 15, wherein the outer diameter of said outer body portion is greater than the outer diameter of said inner body portion.

17. An intraurethral device as defined in claim 1, wherein said second insertion element has a cylindrical shape.

18. An intraurethral incontinent device for use in a female urinary tract comprising:

a urethral plug having a distal end, a proximal end, and a section having a tubular shape, said proximal end having a flange that defines a plug opening, said flange being capable of inhibiting over-insertion of said urethral plug into said urethra, said distal end being adapted to be inserted into a urethra, wherein the shape of said distal end forms a generally concave surface that enables said urethral plug to form a seal with the urethra when inserted therein to substantially inhibit urine leakage from the urethra around said urethral plug;

a first insertion element having an inner surface and an outer surface, said first insertion element containing an elongated element that is configured to be removably inserted through said plug opening; and a second insertion element having an inner surface and an outer surface, said second insertion element defining a channel through which said proximal end of said urethral plug is inserted, wherein said inner surface of said second insertion element is placed adjacent to said outer surface of said first insertion element such that said second insertion element is in operative communication with said first insertion element.

19. An intraurethral device as defined in claim 18, further comprising an enclosure attached to said second insertion element, said enclosure surrounding at least a portion of said urethral plug so that said enclosure is capable of substantially maintaining the sterility of said urethral plug before being inserted into the urethra.

20. An intraurethral device as defined in claim 18, wherein said urethral plug contains an elastomeric material.

21. An intraurethral device as defined in claim 18, wherein said first insertion element further contains an inner body portion having a first end and a second end.

22. An intraurethral device as defined in claim 21, wherein said first end of said inner body portion is connected to said elongated element.

23. An intraurethral device as defined in claim 21, wherein said first insertion element further contains an outer body portion, wherein said second end of said inner body portion is connected to said outer body portion.

24. An intraurethral device as defined in claim 23, wherein said outer body portion and said inner body portion have a cylindrical shape.

25. An intraurethral device as defined in claim 24, wherein the outer diameter of said outer body portion is greater than the outer diameter of said inner body portion.

26. An intraurethral device as defined in claim 18, wherein said second insertion element has a cylindrical shape.

27. A method of substantially inhibiting the leakage of urine from a female urinary tract, said method comprising:

a) providing an intraurethral device, said intraurethral device comprising:
 i) a urethral plug having a distal end and a proximal end, said proximal end defining a plug opening, said distal end being adapted to be inserted into a urethra, said distal end having a certain shape;
 ii) a first insertion element having an inner surface and an outer surface, wherein at least a portion of said first insertion element is removably inserted through said plug opening; and
 iii) a second insertion element having an inner surface and an outer surface, said second insertion element defining an opening through which said proximal end of said urethral plug is inserted, wherein said inner surface of said second insertion element is placed adjacent to said outer surface of said first insertion element such that said second insertion element is in operative communication with said first insertion element;

b) aligning said urethral plug with the urethra;

c) inserting said urethral plug into the urethra according to the following steps:
 i) moving said first insertion element in a direction towards the urethra; and
 ii) thereafter moving said second insertion element in a direction away from the urethra to substantially release the flange from said second insertion element;

d) removing said portion of said first insertion element from said plug opening; and wherein said certain shape of said distal end of said urethral plug enables said urethral plug to form a seal with the urethra to substantially inhibit urine leakage from the urethra around said urethral plug.

28. A method as defined in claim 27, wherein said urethral plug contains an elastomeric material.

29. A method as defined in claim 27, wherein the shape of said distal end forms a generally concave surface.

30. A method as defined in claim 27, further comprising an enclosure that surrounds at least a portion of said urethral plug so that said enclosure is capable of substantially maintaining the sterility of said urethral plug before being inserted into the urethra.

31. A method as defined in claim 30, wherein said enclosure comprises a roll-out nipple.

32. A method as defined in claim 30, wherein said enclosure is attached to said second insertion element.

33. A method as defined in claim 27, wherein said urethral plug further comprises a section having a tubular shape that connects said distal end and said proximal end of said urethral plug.

34. A method as defined in claim 27, wherein said first insertion element contains an elongated element that is configured to be removably inserted through said plug opening.

35. A method as defined in claim 34, wherein said first insertion element further contains an inner body portion having a first end and a second end.

36. A method as defined in claim 35, wherein said first end of said inner body portion is connected to said elongated element.

37. A method as defined in claim 35, wherein said first insertion element further contains an outer body portion, wherein said second end of said inner body portion is connected to said outer body portion.

38. A method as defined in claim 37, wherein said outer body portion and said inner body portion have a cylindrical shape.

39. A method as defined in claim 38, wherein the outer diameter of said outer body portion is greater than the outer diameter of said inner body portion.

40. A method as defined in claim 27, wherein said second insertion element has a cylindrical shape.

41. A method as defined in claim 27, wherein said proximal end of said urethral plug contains a flange that is capable of inhibiting over-insertion of said urethral plug into said urethra.

* * * * *

UNITED STATES PATENT AND TRADEMARK OFFICE
CERTIFICATE OF CORRECTION

| | | |
|---|---|---|
| PATENT NO. | : 6,558,312 B2 | Page 1 of 1 |
| APPLICATION NO. | : 09/805581 | |
| DATED | : May 6, 2003 | |
| INVENTOR(S) | : Robert A. Latour, Jr. | |

It is certified that error appears in the above-identified patent and that said Letters Patent is hereby corrected as shown below:

Title Page; The following references need to be added to the References Cited section of the patent: Please insert;

| | | |
|---|---|---|
| 5,476,434 | 12/1995 | Kalb et al. |
| 5,724,994 | 3/1998 | Simon et al. |
| 6,142,928 | 11/2000 | Zunker et al. |
| 6,440,060 | 8/2002 | Latour, Jr. |

Signed and Sealed this

Twenty-second Day of May, 2007

JON W. DUDAS
*Director of the United States Patent and Trademark Office*